United States Patent [19]

Pecak

[11] 3,962,126

[45] June 8, 1976

[54] REACTIVATION OF A MAGNESIUM OXIDE CATALYST

[75] Inventor: William Eugene Pecak, Cohoes, N.Y.

[73] Assignee: General Electric Company, Pittsfield, Mass.

[22] Filed: Nov. 25, 1974

[21] Appl. No.: 527,139

[52] U.S. Cl. .................. 252/416; 252/420; 260/620; 260/621 R

[51] Int. Cl.² .................. B01J 21/20; B01J 31/06

[58] Field of Search .................. 252/420, 416; 260/621 R, 620

[56] References Cited

UNITED STATES PATENTS

| | | | |
|---|---|---|---|
| 2,414,736 | 1/1947 | Gray | 252/420 |
| 3,446,856 | 5/1969 | Hamilton, Jr. | 260/620 |
| 3,492,083 | 1/1970 | Lowicki et al. | 252/420 |
| 3,764,630 | 10/1973 | Van Sorge | 260/621 R |
| 3,803,249 | 4/1974 | Rieve | 260/621 R |
| 3,867,466 | 2/1975 | Endou et al. | 260/621 R |
| 3,873,628 | 3/1975 | Van Sorge | 260/621 R |

*Primary Examiner*—Winston A. Douglas
*Assistant Examiner*—P. E. Konopka
*Attorney, Agent, or Firm*—William F. Mufatti; Edward A. Hedman; James V. Costigan

[57] ABSTRACT

A improved method of reactivating a magnesium oxide catalyst is disclosed which comprises contacting the catalyst with water after heating the catalyst.

12 Claims, No Drawings

REACTIVATION OF A MAGNESIUM OXIDE CATALYST

This invention relates to an improved method of reactivating a magnesium oxide catalyst which employs the use of water with which the catalyst is contacted after it is heated.

BACKGROUND OF THE INVENTION

Hamilton, U.S. Pat. No. 3,446,856 discloses an alkylation procedure for methylating the ortho position of phenol. This procedure is a vapor phase reaction of a phenol with methanol in the presence of a magnesium oxide catalyst, at a catalyst bed temperature of 475° to 600°C. The service life of the Hamilton catalyst has been relatively short due to the high temperature at which the reaction takes place. It has also been found that the selectivity of the Hamilton catalyst with respect to methanol has been in the range of 40 to 50%. In commonly assigned U.S. patent application Ser. No. 114,698 of Bernardus J. Van Sorge, which is incorporated by reference, there is disclosed a manganese oxide-magnesium oxide catalyst which has extended service life and has a greater degree of selectivity than the Hamilton catalyst. Magnesium oxide catalysts are however subject to carbonization (coking) and eventually these catalysts must be reactivated. The standard procedure for reactivating magnesium oxide catalysts has been based on heating the carbonized catalyst in an atmosphere that contains oxygen. This procedure has partially reactivated the catalyst but not to the extent where the regenerated catalyst was as active as freshly prepared catalyst.

Accordingly, it is a principal object of this invention to provide an improved method of reactivating a magnesium oxide catalyst.

It is also an object of this invention to provide a method for the reactivation of a magnesium oxide catalyst that is capable of restoring the catalytic activity to the level of activity possessed by a freshly prepared catalyst.

DETAILED DESCRIPTION OF THE INVENTION

There is provided a method of reactivating a carbonized magnesium oxide catalyst which comprises exposing the catalyst to heat and thereafter contacting the catalyst with water.

The heating procedure is well known in the art and it is conducted in the presence of an oxygen containing atmosphere to burn off the carbon which coats the carbonized catalyst. The temperature at which this is done is not critical and temperatures between 200°C and 800°C may be employed. As an oxygen containing atmosphere, air or oxygen depleted air may be used. Mixtures of 0.75–2% of oxygen with nitrogen are preferred. However, pure oxygen or mixtures of oxygen with inert gases may be used if desired. After the heating procedure, the catalyst may be contacted with water by immersing the heat treated catalyst in a bath of water. This may be done with or without cooling. Also, it is possible to contact the catalyst with water in the form of steam which is passed through a packed bed or column of the heat treated catalyst. If steam is used, the temperature must not exceed a point which will deactivate the catalyst. When using steam, temperatures should be kept below 300°C.

The amount of water employed is not critical and it is only necessary to use an amount of water which is sufficient to restore the catalytic activity to the level of activity possessed by a freshly prepared catalyst. It is usually convenient to use a 1:10 to a 10:1 weight ratio of water to catalyst, although a larger or smaller amount may be employed.

The magnesium oxide catalyst of Hamilton may be reactivated according to this invention or other promoted magnesium oxide catalyst may be employed. These promoted magnesium oxide catalysts include those which contain molybdenum, tellurium, manganese sulfate and most preferably manganese oxide. U.S. Pat. No. 3,751,488, which is incorporated by reference, describes various molybdenum-magnesium oxide catalysts. Copending Ser. No. 142,798, which is incorporated by reference discloses a magnesium oxide-manganese sulfate catalyst. The tellurium promoted catalysts are described in U.S. Pat. No. 3,707,569 which is also incorporated by reference. The manganese oxide promoted catalysts are disclosed in U.S. patent application Ser. No. 114,698 which is also incorporated by reference.

The manganese oxide component of the manganese oxide promoted magnesium oxide catalyst may be manganese oxide, dimanganese trioxide, trimanganese tetroxide, manganese heptoxide and mixtures thereof. Optimum results have been attained in the regeneration of a pelletized, dimanganese trioxide-magnesium oxide catalyst that contained 3–5% by weight of dimanganese trioxide.

These catalysts may be prepared by blending magnesium oxide with dimanganese trioxide followed by wetting, pelletizing and drying. These procedures are fully described in U.S. patent application Ser. No. 114,698 or U.S. Pat. No. 3,751,488.

DESCRIPTION OF THE PREFERRED EMBODIMENTS

In order that those skilled in the art may better understand the invention, the following examples are given by way of illustration and not by way of limitation.

EXAMPLE I 200 grams of carbonized 3/16 in. dimanganese trioxide-magnesium oxide catalyst pellets containing 3–5% by weight of dimanganese trioxide was heated at a temperature of 650°F for 24 hours in a 2% oxygen – 98% nitrogen atmosphere, to burn off the carbon. Thereafter, the pellets were immersed in water. A strongly exothermic reaction took place as indicated by the evolution of gas and heat. In about 15 minutes, the water temperature reached the boiling point. Subsequent to the completion of the exotherm, the catalyst was isolated and dried for 1 hour at 150°C to remove excess moisture.

This catalyst was charged into a reactor and phenol was selectively methylated with methanol to form 2,6-xylenol. A control reaction was also run using fresh, unused catalyst from the same lot as the reactivated catalyst. The conditions under which both reactions were made were identical, that is the feed composition, liquid hourly space velocity, temperature profile and volume of catalyst charge per reactor. The molar feed ratios of methanol: phenol: O-cresol were 4:0.7:0.3 + 3% $H_2O$ by weight. The LHSV was 2.0/hr. and the volume of catalyst charge was 110 ml. Samples of the reaction produce were obtained at various time intervals during the reaction, and analyzed by gas chromatography. The results are reported in Table 1.

TABLE 1

| | % 2,6-xylenol at Reaction Time (hours) | | | |
|---|---|---|---|---|
| | 15.5 | 18.5 | 67.5 | 88.5 |
| Hydrated Reactivated Catalyst | 56.0 | 57.0 | 59.9 | 56.7 |
| Unhydrated Reactivated Catalyst* | 26.5 | 24.7 | 22.4 | 20.5 |

*Control

EXAMPLE 2

A carbonized dimanganese trioxide-magnesium oxide catalyst was heated according to the method of Example 1 and placed in a 2 in. tube that was 10 feet long. Steam was passed through the tube at a temperature of 150°C for 50 minutes. Thereafter, phenol was alkylated with methanol in the presence of fresh catalyst, unhydrated regenerated catalyst and the hydrated regenerated catalyst according to the present invention. The same reaction conditions were employed as were used in Example 1. The results are shown in Table 2.

CONTROL EXAMPLE

The use of steam at high temperature is not an effective method of magnesium oxide catalyst reactivation. A sample of regenerated catalyst was steam hydrated at 600°F. This catalyst was charged into a reactor and a reaction was carried out. A control reaction was made using the same, but unhydrated catalyst. Both reactions were made concurrently and under identical reaction conditions. The results indicate that steam hydration at 600°F is detrimental to the activity of regenerated catalyst.

| Sample No. | Hours into Reaction | Reaction Temp. °C | % 2,6-xylenol in product Unhydrated Control | Hydrated at 600°F |
|---|---|---|---|---|
| 10 | 13.5 | 475 | 36.3 | 33.6 |
| 11 | 16. | 475 | 34.1 | 32.1 |

Although the above examples have shown various modifications and variations of the present invention, other modifications and variations are possible in light of the above teachings. It is, therefore, to be understood that changes may be made in the particular embodiments of the invention described which are within the full intended scope of the invention as defined by the appended claims.

I claim:

1. In the method of reactivating a carbonized magnesium oxide catalyst that has become carbonized by use in a phenol alkylation reaction which comprises burning carbon from said catalyst by exposing said catalyst to heat in an oxygen containing atmosphere, to form a partially reactivated catalyst the improvement which consists essentially of contacting said partially reactivated catalyst with a sufficient amount of water at a temperature below 300 °C to restore the activity of said catalyst.

2. The method of claim 1 wherein said partially reactivated catalyst is contacted with water by immersion.

3. The method of claim 1 wherein said partially reactivated catalyst is contacted with water in the form of steam.

4. The method of claim 1 wherein said partially reactivated catalyst contains a promoter.

5. The method of claim 4 wherein the promoter is a manganese oxide.

6. The method of claim 5 wherein the manganese oxide is selected from the group consisting of manganese oxide, dimanganese trioxide, trimanganese tetroxide, manganese heptoxide and mixtures thereof.

7. The method of claim 6 wherein the manganese oxide is dimanganese trioxide.

8. In a method of reactivating a carbonized magnesium oxide catalyst that has become carbonized by use in catalyzing the vapor phase ortho methylolation of phenol with methanol by exposing said carbonized magnesium oxide catalyst to a temperature of from 200° to 800°C in an oxygen containing atmosphere to form partially reactivated catalyst, the improvement which consists essentially of contacting said partially reactivated catalyst with water at a temperature below 300°C at a 1:10 to a 10:1 weight ratio of water to catalyst to restore the catalytic activity to the level of activity possessed by a freshly prepared catalyst.

9. The method of claim 8 wherein the partially reactivated catalyst is contacted with water by immersion.

10. The method of claim 8 wherein the partially reactivated catalyst is contacted with water in the form of steam.

11. The method of claim 10 wherein the catalyst also includes a manganese oxide selected from the group consisting of manganese oxide, dimanganese trioxide, trimanganese tetroxide, manganese heptoxide and mixtures thereof.

12. The method of claim 11 wherein the manganese oxide is dimanganese trioxide.

* * * * *